(12) United States Patent
Jayaraman et al.

(10) Patent No.: US 10,772,569 B2
(45) Date of Patent: Sep. 15, 2020

(54) DEVICE AND METHOD TO DETECT DIABETES IN A PERSON USING PULSE PALPATION SIGNAL

(71) Applicant: Tata Consultancy Services Limited, Mumbai (IN)

(72) Inventors: Srinivasan Jayaraman, Bangalore (IN); Naveen Kumar Thokala, Bangalore (IN); Balamuralidhar Purushothaman, Bangalore (IN)

(73) Assignee: Tata Consultancy Services Limited, Mumbai (IN)

( * ) Notice: Subject to any disclaimer, the term of this patent is extended or adjusted under 35 U.S.C. 154(b) by 503 days.

(21) Appl. No.: 15/356,000

(22) Filed: Nov. 18, 2016

(65) Prior Publication Data

US 2017/0143279 A1    May 25, 2017

(30) Foreign Application Priority Data

Nov. 20, 2015 (IN) .......................... 4372/MUM/2015

(51) Int. Cl.
*A61B 5/00* (2006.01)
*G16H 50/20* (2018.01)
(Continued)

(52) U.S. Cl.
CPC ........ *A61B 5/7275* (2013.01); *A61B 5/02116* (2013.01); *A61B 5/02405* (2013.01); *A61B 5/02416* (2013.01); *A61B 5/4842* (2013.01); *A61B 5/4854* (2013.01); *A61B 5/4866* (2013.01); *A61B 5/681* (2013.01);
(Continued)

(58) Field of Classification Search
CPC ..... A61B 5/7275; A61B 5/7246; G16H 50/20
See application file for complete search history.

(56) References Cited

U.S. PATENT DOCUMENTS 5,741,211 A     4/1998  Renirie et al.
2007/0255122 A1  11/2007  Vol et al.
(Continued)

OTHER PUBLICATIONS

Velik, R., "An Objective Review of Technological Developments for Radial Pulse Diagnosis in Traditional Chinese Medicine", European Journal of Integrative Medicine, vol. 7, Issue 4, 25 pgs., Jul. 2015.

*Primary Examiner* — Hien N Nguyen
(74) *Attorney, Agent, or Firm* — Finnegan, Henderson, Farabow, Garrett & Dunner, LLP

(57) ABSTRACT

A device and method is provided for the detection of diabetes in a person using pulse palpation signals. The pulse palpation signal is captured from the radial artery of the person using a photo-plethysmograph (PPG) sensor. The PPG signal is then preprocessed by a processor. The preprocessed PPG signal is then analyzed by the processor to detect the peak in the PPG signal. The detected peaks are used to extract a first set of feature parameters. The first of feature parameters are compared with a second set of feature parameters, wherein the second set of feature parameters are extracted from the control group of individuals. Based on the comparison it is detected that the person is one of in normal condition, pre-diabetic condition or a diabetic condition. According to another embodiment, the invention also provides a method to determine the severity index and progression risk of diabetes in the person.

13 Claims, 6 Drawing Sheets

(51) Int. Cl.
    *A61B 5/024*     (2006.01)
    *A61B 5/021*     (2006.01)
    *G16H 50/30*     (2018.01)
    *G16H 50/70*     (2018.01)
    *G16H 40/63*     (2018.01)

(52) U.S. Cl.
    CPC .......... *A61B 5/6824* (2013.01); *A61B 5/7203* (2013.01); *A61B 5/7225* (2013.01); *A61B 5/7246* (2013.01); *A61B 5/7264* (2013.01); *A61B 5/7267* (2013.01); *G16H 40/63* (2018.01); *G16H 50/20* (2018.01); *G16H 50/30* (2018.01); *G16H 50/70* (2018.01); *A61B 5/0053* (2013.01)

(56) References Cited

U.S. PATENT DOCUMENTS

| | | |
|---|---|---|
| 2008/0306357 A1 | 12/2008 | Korman |
| 2015/0196705 A1 | 7/2015 | Brenneman et al. |
| 2017/0079533 A1* | 3/2017 | Robinson ............ A61B 5/02007 |
| 2017/0164904 A1* | 6/2017 | Kirenko ............... A61B 5/7214 |

* cited by examiner

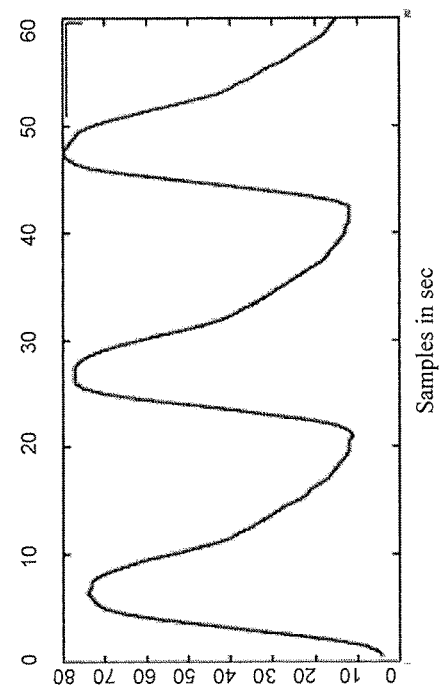
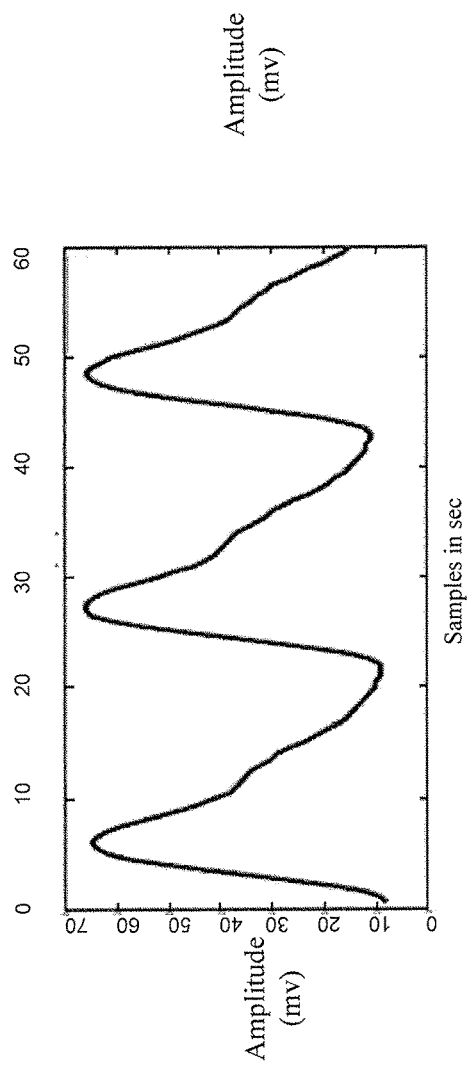
FIG. 4

DEVICE AND METHOD TO DETECT DIABETES IN A PERSON USING PULSE PALPATION SIGNAL

CROSS-REFERENCE TO RELATED APPLICATIONS AND PRIORITY

The present application claims priority from Indian provisional specification no. 4372/MUM/2015 filed on 20 Nov. 2015, the complete disclosure of which, in its entirety is herein incorporated by references.

TECHNICAL FIELD

The present application generally relates to diabetes detection in a person. More particularly, but not specifically, the invention is related to a method and system for the detection of diabetes in the person using a pulse palpation signal captured from the person.

BACKGROUND

Diabetes mellitus (DM) is one of the most common diseases now a day. Diabetes consists of malfunction of glucose-insulin regulatory system leading to the onset various complications. As per a prediction made World Health Organizations report (WHO/NMH/MNC/03.1), there will be at least 350 million people in the world with type 2 diabetes by the year 2030. Therefore it becomes essential to screen people for diabetes on a regular basis. Further it is uncertain that whether such screen may be done at a population wide basis or just for people who can be shown to have high risk. It is also uncertain at what age the diabetes screening program should be initiated. Furthermore such screening also proves beneficial for assessment of long term health condition risks like type 2 diabetes, heart disease, hypertension, stroke, kidney disease, some forms of dementia such as Alzheimer's and so on. Also, continuous monitoring of diabetes patients can aid in assisting the short and long-term complication risks as well.

A majority of existing solutions for such monitoring relies on techniques such as C-peptide test, fasting plasma glucose test, GAD antibodies test, Hba 1c test, oral glucose tolerance test, type-2 diabetes indication test. It should be noted that most of the above-mentioned technique are either invasive or minimal invasive (figure prick) in nature. Further, based on the blood glucose level an individual will be mapped with normal, pre-diabetic or diabetic. Furthermore the sensors used in the above techniques may be uncomfortable for the patient and are typically used no more than three or four times a day.

The prior art literature does not explore non-invasive methods of diabetic screening further none of the prior art discloses methods to continuously monitor the vulnerability of an individual towards diabetes so as to determine the severity index of the disease and estimate the health condition risk due to diabetes.

Some prior art have vaguely considered Pulse wave analysis to be a simple, noninvasive and informative technique for arterial assessment in which the central arterial blood pressure can be estimated from the Brachial Blood Pressure. However, the prior art literature does not reach a consensus regarding the validity of the technique. Instead, Murgo et al (1980; 62:105-116) teaches that the shape of the arterial pulse will be affected by the changes in the peripheral circulation or alterations in cardiac function.

Prior art literature have illustrated various method of determining and screening of diabetes, however, continuous and non-invasive screening of diabetes is still considered as one of the biggest challenges of the technical domain.

SUMMARY

Embodiments of the present disclosure present technological improvements as solutions to one or more of the above-mentioned technical problems recognized by the inventors in conventional systems.

The present application provides a device for the detection of diabetes in a person in accordance with an embodiment of the invention. The device uses a non-invasive pulse palpation detection technique from arterial tree of a person for the detection of diabetes in the person. The device can acquire or collect the pulse signal either by mean of existing device or specially designed device. The present invention is using an approach inspired from ancient Indian traditional medicine (Nadi diagnosis approach). The device includes a sensor, a processor, a memory and a data-storage operatively coupled with the processor.

In an embodiment of the invention, the sensor is a PPG sensor configured to generate a PPG signal from the fingertip arteries of the person. The PPG signal is then processed by the processor to generate preprocessed PPG signal. The preprocessed signal is further analyzed to extract first set of feature parameters. The first set of feature parameters are extracted using peak detection technique. The first set of parameters are then compared with a second set of feature parameters, wherein the second set of feature parameters are extracted from a control group of individuals. Based on the comparison of the first set of feature parameters and the second set of feature parameters, the person can be classified as one of in normal condition, pre-diabetic condition or a diabetic condition.

According to another embodiment a processor implemented method is also provided for the detection of diabetes in the person using the above mentioned device.

In another embodiment, a non-transitory computer-readable medium having embodied thereon a computer program for detection of diabetes in the person. Initially, a signal is acquired by monitoring the arterial palpation of the person using a plurality of sensors. At the next step the signal is preprocessed to generate a preprocessed signal. A plurality of peaks are then detected by the processor from the preprocessed signal. In the next step, a first set of feature parameters are extracted from the plurality of peaks. In the next step, the first set of parameters are compared by the processor with a second set of parameters. The second set of parameters are extracted from a control group of individuals. Finally, it was detected by the processor whether the person is in at least one of a normal, a pre-diabetic or diabetic condition based on the comparison.

BRIEF OF DESCRIPTION OF THE DRAWINGS

The foregoing summary, as well as the following detailed description of preferred embodiments, are better understood when read in conjunction with the appended drawings. For the purpose of illustrating the invention, there is shown in the drawings exemplary constructions of the invention; however, the invention is not limited to the specific methods and system disclosed. In the drawings:

FIG. 4 shows a PPG signal received from the control group of individuals and the person, in accordance with an embodiment of the present disclosure;

DETAILED DESCRIPTION OF THE INVENTION

Figure 1:
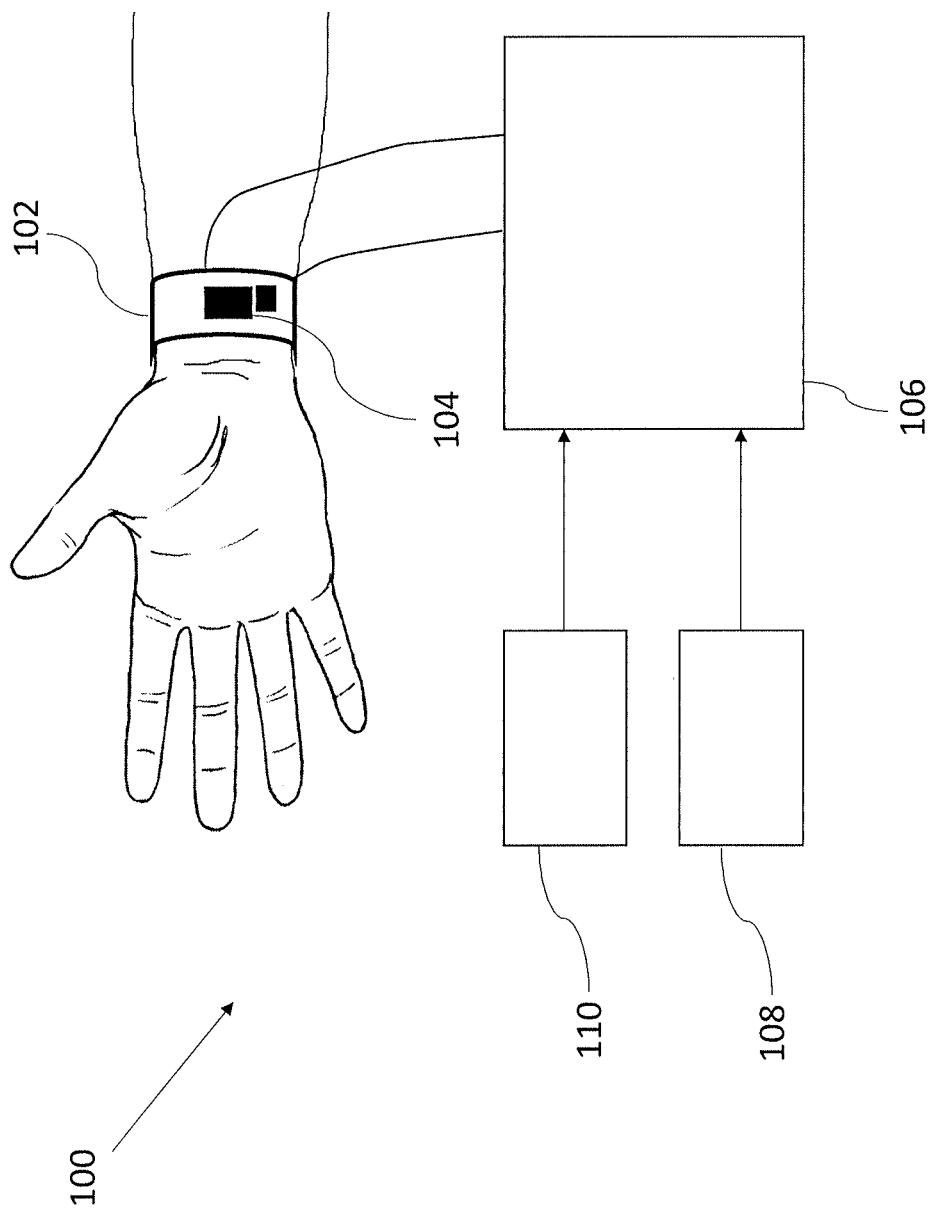
FIG. 1 shows a schematic block diagram of a system for the detection of diabetes in a person, in accordance with an embodiment of the invention.

Some embodiments of this invention, illustrating all its features, will now be discussed in detail.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present invention, the preferred, systems and methods are now described. In the following description for the purpose of explanation and understanding reference has been made to numerous embodiments for which the intent is not to limit the scope of the invention.

One or more components of the invention are described as module for the understanding of the specification. For example, a module may include self-contained component in a hardware circuit comprising of logical gate, semiconductor device, integrated circuits or any other discrete component. The module may also be a part of any software programme executed by any hardware entity for example processor. The implementation of module as a software programme may include a set of logical instructions to be executed by a processor or any other hardware entity.

The disclosed embodiments are merely exemplary of the invention, which may be embodied in various forms.

The elements illustrated in the Figures interoperate as explained in more detail below. Before setting forth the detailed explanation, however, it is noted that all of the discussion below, regardless of the particular implementation being described, is exemplary in nature, rather than limiting. For example, although selected aspects, features, or components of the implementations are depicted as being stored in memories, all or part of the systems and methods consistent with the attrition warning system and method may be stored on, distributed across, or read from other machine-readable media.

Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk.

FIG. 1 illustrates a schematic block diagram of a device 100 for the detection of diabetes in a person in accordance with an embodiment of this invention. The device 100 uses a non-invasive pulse palpation detection technique for the detection of diabetes in the person. The device 100 can acquire or collect the pulse signal either by mean of existing device or specially designed device. The present invention is using an approach inspired from ancient Indian traditional medicine (Nadi diagnosis approach). However, the sensing the technique adapted by the Nadi is different from the PPG based approach.

According to an illustrative embodiment of the invention, the device 100 includes a strap 102, at least one sensor 104 present on the strap 102, a processor 106, a memory 108 and a data-storage 110 as shown in FIG. 1. The sensor 104 is configured to measure or monitor the arterial pulse at the fingertip of the person. In an embodiment, a pulse sensor 104 is used as the sensor 104. The pulse sensor 104 is configured to collect the signal for minimum of one minute of arterial pulse. It should be appreciated that, the pulse sensor 104 may use an optical sensor similar to photo-plethysmography (PPG) for monitoring the arterial pulse at the wrist or any other part of the body. It should also be appreciated that the pulse sensor 104 may use pressure sensor for monitoring the arterial pulse at the wrist or any other part of the body. It should further be appreciated that the pulse sensor 104 may use displacement sensor for monitoring the arterial pulse at the wrist or any other part of the body. For the sake of clarity in this disclosure, the pulse sensor 104 and the PPG sensor 104 will be replaceable. The PPG sensor 104 is configured to generate a PPG signal. The PPG signal is then sent to the processor 106.

The processor 106 is electronically coupled with the memory 108 and the data-storage 110. The processor 106 is configured to take the PPG signal as an input from the sensor 104 to generate a pre-processed PPG signal. The processor 106 is further configured to extract a first set of feature parameters from the pre-processed PPG signal using a peak detection technique. The first set of extracted feature parameters may be stored in the data storage 110 of the device 100 and may be used for further processing. The memory element may store various programmed instructions to be performed by the processor 106. The processor 106 is further configured to match the first set of feature parameters from the person with the second set of feature parameters from the probe phase by implementing machine learning techniques to classify the person as normal, pre-diabetic or diabetic.

Figure 2:
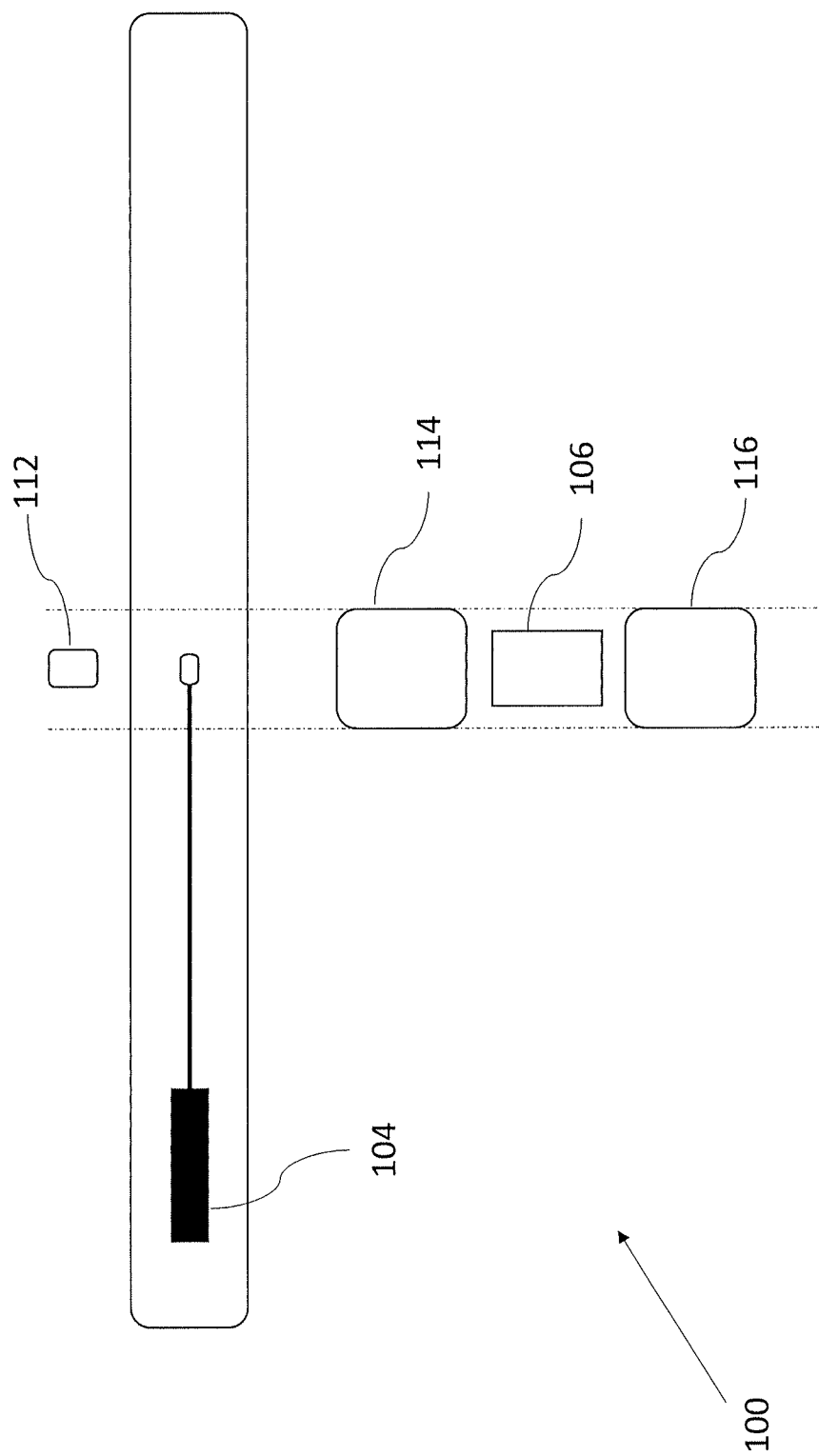
FIG. 2 shows a wearable sensor for the detection of diabetes by sensing an arterial pulse palpation rate in the wrist, in accordance with an embodiment of the present disclosure.

An exploded view of the wearable sensor 104 for detection of diabetes in the person shown in FIG. 2. The figure shows the wearable sensor 104 including a screw 112, an upper cover 114, a lower cover 116 and the processor 106 which can be fitted between the upper cover 114 and the lower cover 116.

In another embodiment, the physiological data or signals may be captured by using non-invasive method using one or more sensors. In an embodiment the sensor may be attached to a wrist or a fingertip or any part of body of the human being, where the arterial pulse can be sensed (peripheral organs). For example, a wrist watch or a wristband or a textile material such as cuff can be used to measure the arterial pulse palpation signals or biological parameter, or a ring or finger-cap to measure arterial pulse at the finger-tip. In one aspect, the arterial pulse palpation signals are captured, from at least one external sensor, for a predetermined ultra-short or short duration.

Figure 3:
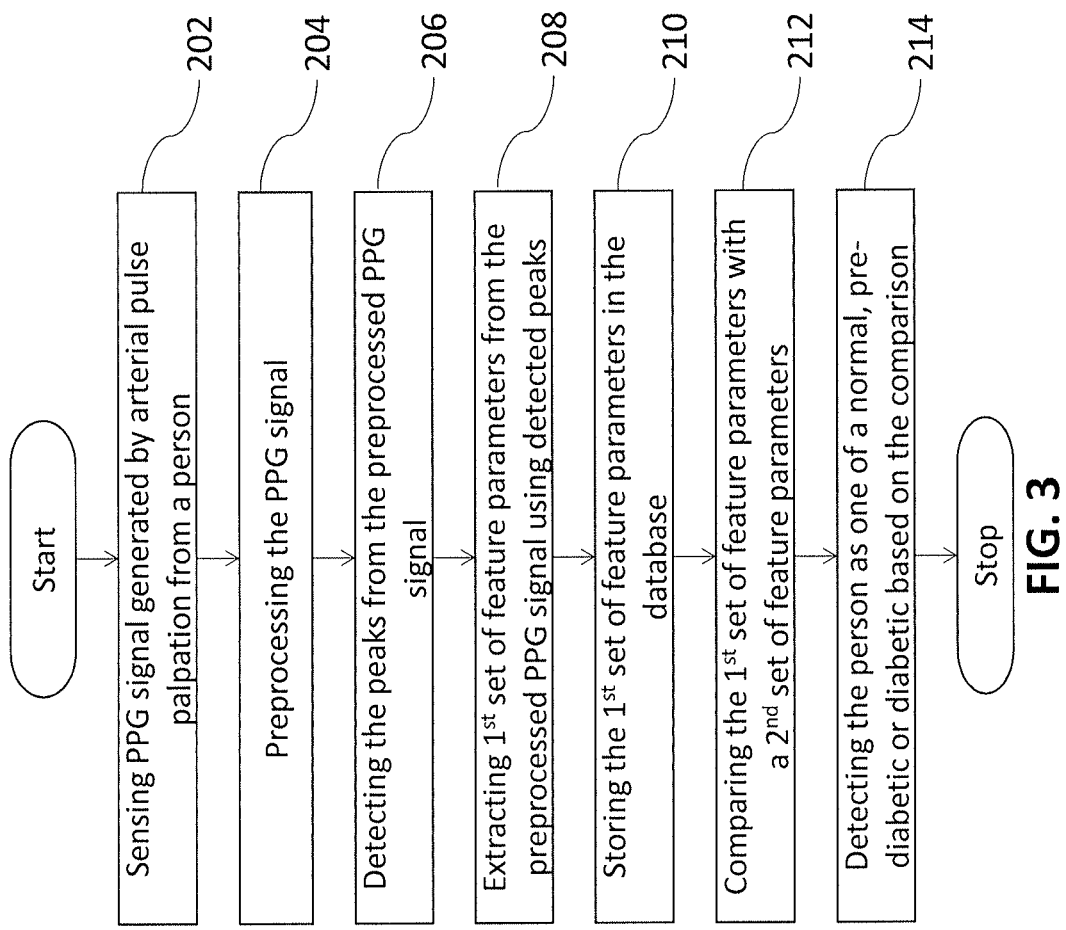
FIG. 3 shows a flowchart illustrating steps involved in detection of diabetes in the person, in accordance with an embodiment of the invention.

Referring to FIG. 3 is a flow chart 200 illustrating the steps involved in the detection of diabetes in a person. Initially, at step 202, where a pulse signal is sensed by the PPG sensor 104. In an embodiment the PPG signal may be acquired by monitoring the arterial pulse palpation of the person. In the next step 204, the acquired PPG signal is processed to produce the preprocessed PPG signal. In an embodiment, preprocessing of the PPG signal includes amplifying the PPG signal, to produce an amplified PPG signal, filtering any noise from the amplified PPG signal to produce a filtered PPG signal and sampling the filtered PPG signal at a predefined frequency to produce the preprocessed PPG signal.

In an embodiment the PPG signal is amplified due to the extremely low magnitude of the initially acquired PPG signal. In another embodiment the filtering of the amplified PPG signal is performed to remove noise from the amplified PPG signal. In another embodiment the sampling of the filtered PPG signal may be performed by using an Analog digital convertor (ADC). In yet another an embodiment the predefined frequency for sampling the filtered PPG signal may be 60 Hz.

In the next step 206, a plurality of peaks is detected from the preprocessed PPG signal. At step 208, the first set of feature parameters are extracted from the preprocessed PPG signal using the detected peaks. The feature extraction result in the extraction of a first set of feature parameters of the person. At step 210, the extracted first set of feature parameters are stored in the data storage 110 for future processing by the device. In the next step 212, the first set of feature parameters are compared with a second set of feature parameters extracted from a control group of individuals. The control group of individuals includes individuals with known classification as normal, pre diabetic or diabetic. The first set of feature parameters and the second set of feature parameters are matched using at least one of machine learning techniques to classify a person as Normal, pre-diabetic or diabetic. And finally at step 214, it is detected that the person is at least one of a normal, pre-diabetic or a diabetic.

According to another embodiment of the invention, the step of feature extraction further involves various steps as follows: the PPG signal contains a slowly varying DC (due to breathing) and other high frequency noise components. However, the fundamental frequency lies between 1 to 1.5 Hz based on the heart rate of a person (60-90 bpm). Raw PPG signal is shifted to its zero mean and filtered using a $2^{nd}$ order Butterworth band-pass filter having cutoff frequencies of 0.5 Hz and 20 Hz to remove the undesired frequency components.

According to another embodiment of the invention, the filtered PPG signals are then processed and peaks are detected from $s_1, s_2 \ldots$ wherein $s_n$ are the various individuals PPG Signal. The distance between the consecutive peaks are calculated and represented as:

$$PP = \{PP_1, PP_2, \ldots PP_n\}$$

From the set of different peaks, different kind of features are calculated. Temporal features (like mean of the peaks, standard deviation etc.) shape based, Entropy and frequency based features.

Mean of PP intervals (mean PP), standard deviation of the normal-to-normal PP intervals (SDNN), root mean square of successive differences between adjacent PP intervals (RMSSD) and the percentage of number of PP intervals with differences >50 ms (pNN50) were calculated in the time-domain. Frequency-domain measures were obtained by fast Fourier transformation and they included the absolute powers obtained by integrating the powers in the very low frequency (VLF) band of 0.0033-0.04 Hz, low frequency (LF) band of 0.04-0.15 Hz, high frequency (HF) band of 0.15-0.4 Hz, and the total power in all the 3 bands together. The normalized units (nu) of LF and HF power, as well as the LF/HF ratio, were considered. For example in Frequency based Feature extraction from PPG's PP—interval vector. The power spectra of HRV and PRV were calculated using a Welch's periodogram method (50% overlapping). The pulse interval series were converted to an even time sampled signal by cubic spline interpolation. A Blackman window was applied to each segment and the fast Fourier transform was calculated for each windowed segment. Finally, the power spectra of the segments were averaged.

From spectral analysis, two frequency bands were considered: low frequency (LF) band (0.045-0.15 Hz) and high frequency (HF) band (0.15-0.4 Hz). The very low frequency (VLF) band was not taken into account because the physiological correlates are still unknown. Band spectral power was computed as the sum of the products of power spectrum densities of the band harmonics by the sharpness of the spectrum. Here, LF and HF oscillatory components are presented in absolute (square milliseconds, ms2) units, and the LF/HF ratio is also displayed. HF is also presented in normalized units (nu), Obtained as follows $$HF_{nu} = \frac{HF}{\text{Total Power} - VLF} \times 100$$

These features are used for developing a classifier that can classify a diabetic individual from a normal individual.

$$F = [PRV_1, PRV_2, \ldots PRV_N]$$

Number of users is 'U'
Number of trials for one user is 'T' and
Feature F of PPG signal is of length 'N'.
Where
i=1, 2 . . . U
j=1, 2 . . . N
k=1, 2 . . . T
The number of individuals forming the part of the control group of individuals is U, the number of time an individual comes for trial is T and length of harmonic corresponding to the time duration for which the PPG signal is acquired is referred to as N.

According to another embodiment of the invention, to validate the results of the present invention, two methods were performed as follows:

A) Statistical Model Approach

Figure 5:
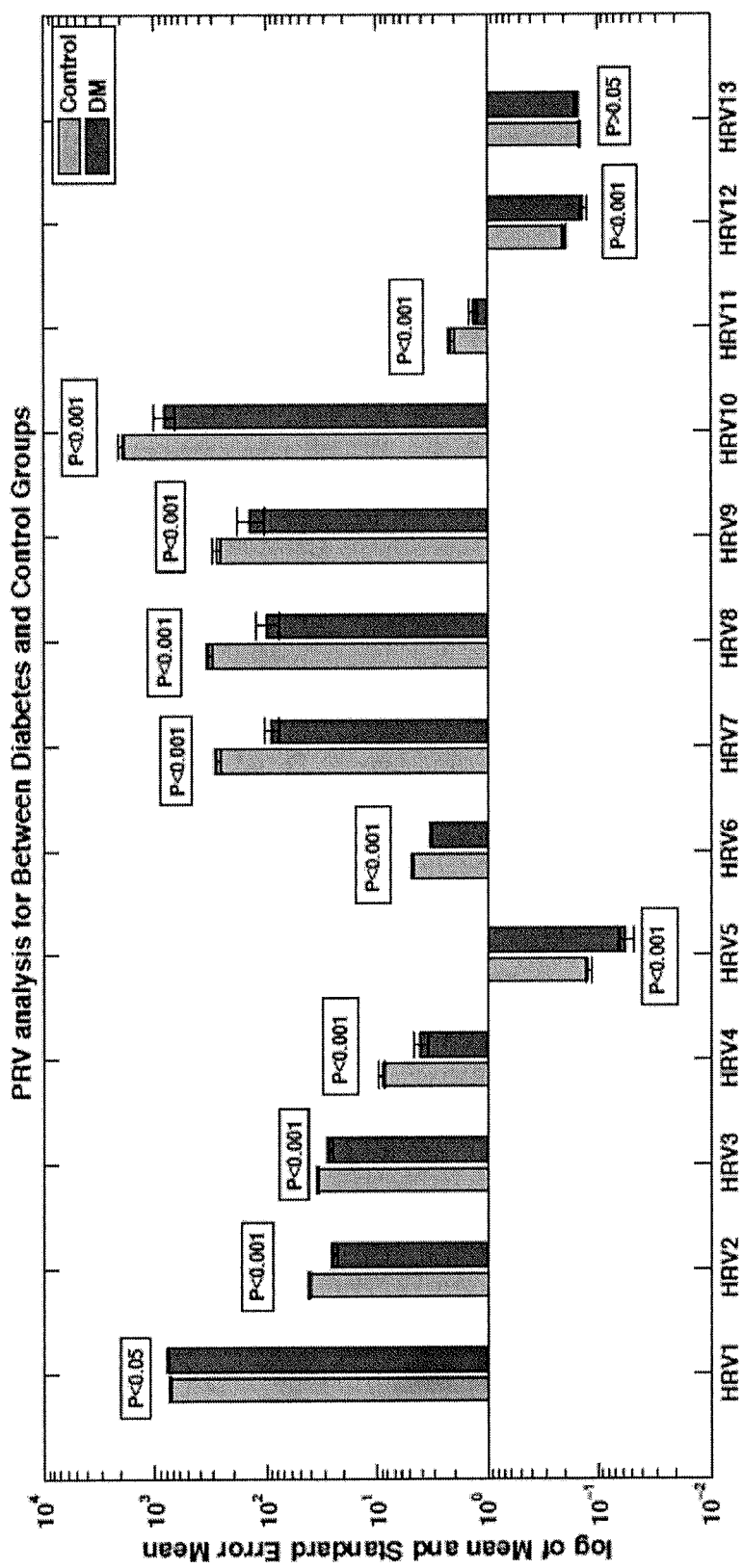
FIG. 5 shows the comparison of the mean and standard error mean of pulse rate variability features of PPG signal for control group of individuals and the person, in accordance with an embodiment of the invention.

Extracted features were processed and used for diabetes detection application. FIG. 5 shows that control group is significantly different from diabetes group. The comparison of the mean and standard error mean of pulse rate variability features of PPG signal for control group of individuals and the person was done.

B) Machine Learning Approach

1. Feature Selection:

The classification can be represented as follows:

$$Y = f(PRV_1, PRV_2, \ldots PRV_n)$$
$$Y = 1 \text{ for normal individual}$$
$$= 0 \text{ for diabetic individual}$$

Novel feature selection algorithm is used for selection of features that are derived from PPG signal. Feature selection is based on the ratio of correlation between the feature, output and sum of correlations with all the other features. Here, x1 represents all features of the input data set and X represents remaining features in the input data set that are not correlated in the previous correlation. The features are pulse rate variability (PRV) that are present in the input data set. All the PRV features in the input data set obtained from the plurality of peaks is correlated with the output that is a function of a pulse rate variability features of a number of users. This is represented as x1. The PRV features that are not correlated with the output is X that are correlated with all the PRV features (x1) in the input data set.

$Cor_{X1,Y}$=correlation ($X_1$, Y) is the correlation between x1 (represents feature in input set) and Y (output)

$Cor_{X1,X}$=correlation ($X_1$, X) is the vector consisting of correlation between x1 and X the remaining features in the input data set.

$$\text{ImpactCoeff} = \text{correlation}(x_1, Y) / \sqrt{(\Sigma \text{correlation}(x_1, X))}$$

This process makes sure that features that are highly correlated with output and least correlated with the other input factors are selected as input feature vector for classification algorithm.

2. Classification Algorithm:

Once feature selection is done, the data is divided into training and testing data. Lot of machine learning algorithms likes artificial neural networks (ANN), logistic regression and support vector machines (SVM) can be used for classification. For simplicity and easy to use, here SVM base classifier has been adapted, as the size of subjects used is small.

$$Y2=f(x1, x2 \ldots xn)$$

Where Y2=1 for normal individuals and 0 for diabetic individuals $$f_r(x, c_i) = \begin{Bmatrix} 1, \text{ for Class } C_1 \\ 0, \text{ for Class } C_2 \end{Bmatrix} \quad (1)$$

x1, x2 . . . xn are the features with high impact coefficient

Figure 6:
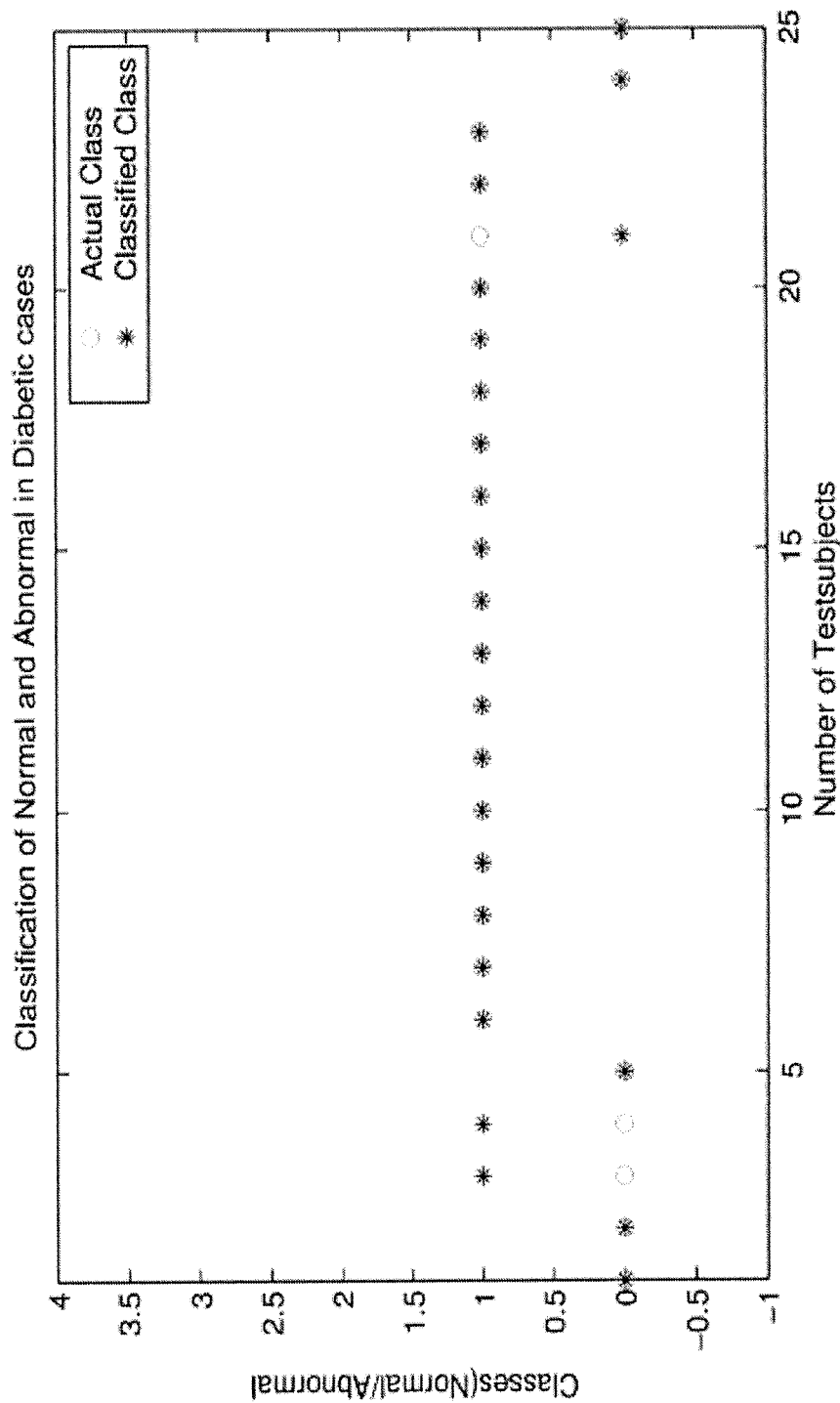
FIG. 6 shows subject wise classification of normal and abnormal in diabetes cases, in accordance with an embodiment of the invention.

The SVM based diabetic classification results can be shown in FIG. 6. The figure shows subject wise classification of normal and abnormal in diabetes cases. The results show that the accuracy of the SVM based diabetic classification is close to 90%.

The invention disclosed herein may further be used to display the results of the classification of the person using a mobile device. The mobile device may be a general mobile device such as a smart phone electronically coupled with the device disclosed herein or may be a specialized device electronically coupled to the device disclosed herein and configured to display the classification of the person.

According to another embodiment of the invention, the mobile device or any other electronic device may further be used to display the processed information regarding the health severity index.

According to another embodiment of the invention, the device 100 can acquire the pulse signal continuously and transmit the signal to a cloud server. The continuous measurement of pulse signal is used for disease management application using a decision support system (DSS). The DSS is also configured to determine the severity index of the diabetes.

According to another embodiment the DSS of the severity index can be estimated by collecting or calculating the PTT/PWV of an individual during a first time instant PTT=x msec.

During next measurement data collected indicates PPT=y msec Where y=x±Δx in that such a case it may be adjudged that if x<y==health is improved
if x>y==Health has to be improved
x=y no improvement According to another embodiment of the invention, the device is also configured to estimate the cardiac condition risk due to diabetes by means of decision fusion approach. In this case, the diabetes information with other physiological parameter will be fused to estimate the cardiac risk due to diabetes.

The disclosed invention may further be incorporated such that the person may store information or preferences as to triggering an alert to a predefined point of contact. In an example an alert may be triggered when the individual is adjudged above a predefined threshold on the severity index. In another example the alert may be triggered when the person is determined as diabetic.

The alert may include sending a distress call to a predefined phone or sending a message to a predefined phone number.

In an embodiment referring to FIG. 4, the raw PPG signals acquired by the sensor 104 may be depicted in the form of amplitude versus Sample in second graph for Control group of individuals during the training phase and the person during the probe phase. Since the PPG signal may be low in magnitude therefore the preprocessing module to the magnitude of 1 mV the processor 106 is configured to amplify the acquired PPG signal.

In another embodiment of the present invention, the processor 106 may be configured to match the first set of feature parameters with the second set of feature parameters to determine the severity index of diabetes disease for the person by matching the training feature parameters with the probe feature parameters.

In another embodiment the processor 106 may further be configured to match the first set of feature parameters with the second set of feature parameters to determine the progression risk of the diabetes disease for the person.

In another embodiment the disclosed invention may collect, record, acquire and other physiological parameters using invasive or imaging technique like blood glucose level or echocardiogram respectively and transmit it to central server or cloud or remote device. The processor 106 may further be configured to fuse the diabetes information obtained by implementing the current invention with other physiological parameters to estimate a cardiac risk to the individual under test.

In view of the foregoing, it will be appreciated that the present invention provides a real time method and device to detect the diabetes in the person by measuring pulse signal of the person using a pulse palpation technique.

What is claimed is:

1. A method for detecting diabetes, the method comprising:
    acquiring a signal by monitoring arterial palpation of a person using a plurality of sensors;
    preprocessing, by a processor, the signal to generate a preprocessed signal;
    detecting by the processor, a plurality of peaks from the preprocessed signal;
    extracting by the processor, a first set of parameters from the plurality of peaks;
    comparing by the processor, the first set of parameters with a second set of parameters, using a machine learning technique that includes selection of features from the signal based on an impact coefficient computed from a ratio of correlation between pulse rate variability features in an input data set of the signal and output being a function of a pulse rate variability features of a number of users, and sum of correlations between the pulse rate variability features in the input data set of the signal with remaining features other than the features correlated in the input data set, and selecting features that are highly correlated with the output and least correlated with the remaining features in the input data set are selected as input feature vector;
    applying classification algorithm to classify the person in one of a normal, a pre-diabetic, or a diabetic condition in accordance with a value of the impact coefficient, wherein the second set of parameters are extracted from a control group of individuals; and
    determining, by the processor, a severity index by collecting a pulse wave velocity (PWV) of the person during a time instant and subsequent time instants to adjudge health of the person with the diabetic condition as one of: improved, to be improved, no improvement.

2. The method of claim 1, wherein the signal is photoplethysmograph (PPG) signal captured from arterial pulse of the person using a photo-plethysmogram.

3. The method of claim 1, wherein the step of preprocessing further comprises,
    amplifying by the processor, the signal to produce an amplified signal,
    removing by the processor, noise from the amplified signal to produce a filtered signal, and
    sampling by the processor the filtered signal into predefined intervals to produce the preprocessed signal.

4. The method of claim 1, wherein the step of extracting the second set of parameters comprises,
    receiving by the processor a training signal from each individual of the control group of individuals;
    pre-processing by the processor, the training signal, wherein the pre-processing includes,
        amplifying, by the processor, the training signal to produce a training amplified signal;
        removing, by the processor, noise from the training amplified signal to produce a filtered signal; and
        sampling by the processor, the training filtered signal into predefined intervals to produce a training preprocessed signal; and
    analyzing, by the processor, the training pre-processed signal, using peak detection for extracting the second set of parameters from the training preprocessed signal.

5. The method of claim 1 further comprising a step of storing the first set of parameters for further processing.

6. The method of claim 1 further comprising sending the signal to at least one of a central server, a remote device, or a cloud server.

7. The method of claim 1 further comprising estimating by the processor, progression risk of diabetes disease.

8. The method of claim 1 further comprising:
    continuously monitoring a value of the pulse wave velocity for the person under test; and
    comparing the pulse wave velocity at two distinct time instants to determine the severity index and progression risk of diabetes disease.

9. A device for detecting diabetes, the device comprising:
    a plurality of sensors configured to acquire a signal by monitoring arterial palpation of a person;
    a processor and a memory coupled to the processor, wherein the processor configured to execute computer readable instructions stored in the memory to:
        preprocess the signal to generate a preprocessed signal;
        detect, a plurality of peaks from the preprocessed signal;
        extract a first set of parameters from the plurality of peaks;
        compare the first set of parameters with a second set of parameters using a machine learning technique that includes selection of features from the signal based on impact coefficient computed from a ratio of correlation between pulse rate variability features, in an input data set of the signal and output being a function of a pulse rate variability features of a number of users, and sum of correlations between the pulse rate variability features in the input data set of the signal with remaining features in the input data set, and selecting features that are highly correlated with the output and least correlated with the remaining features other than the features correlated in the input data set are selected as input feature vector;
        applying classification algorithm to classify the person in one of a normal, a pre-diabetic, or a diabetic condition in accordance with a value of the impact coefficient, wherein the second set of parameters are extracted from a control group of individuals; and
        determine a severity index by collecting a pulse wave velocity (PWV) of the person during a time instant and subsequent time instants to adjudge health of the person with the diabetic condition as one of: improved, to be improved, no improvement.

10. The device of claim 9, wherein the signal is a photo-plethysmograph signal captured from arterial pulse of the person using a photo-plethysmogram.

11. The device of claim 10, wherein the photo-plethysmogram is using a displacement sensor.

12. The device of claim 9 further comprising a mobile device to display the classification of the person as a normal, pre-diabetic or diabetic.

13. A non-transitory computer-readable medium having embodied thereon a computer program configured to detect diabetes, the method comprising:
    acquiring a signal by monitoring arterial palpation of a person using a plurality of sensors;
    preprocessing, by a processor, the signal to generate a preprocessed signal;

detecting, by the processor, a plurality of peaks from the preprocessed signal;
extracting, by the processor, a first set of parameters from the plurality of peaks;
comparing, by the processor, the first set of parameters with a second set of parameters using a machine learning technique that includes selection of features from the signal based on an impact coefficient computed from a ratio of correlation between pulse rate variability features, in an input data set of the signal and output being a function of a pulse rate variability features of a number of users, and sum of correlations between the pulse rate variability features in the input data set of the signal with remaining features other than the features correlated in the input data set, and selecting features that are highly correlated with the output and least correlated with the remaining features in the input data set are selected as input feature vector;
applying classification algorithm to classify the person in one of a normal, a pre-diabetic, or a diabetic condition in accordance with a value of the impact coefficient, wherein the second set of parameters are extracted from a control group of individuals; and
determining, by the processor, a severity index by collecting a pulse wave velocity (PWV) of the person during a time instant and subsequent time instants to adjudge health of the person with the diabetic condition as one of: improved, to be improved, no improvement.

* * * * *